United States Patent [19]

Barr

[11] Patent Number: 5,656,458

[45] Date of Patent: Aug. 12, 1997

[54] EXPRESSION AND PROCESSING OF AMINO TERMINUS ACETYLATED FGF'S IN YEAST

[75] Inventor: Philip J. Barr, Berkeley, Calif.

[73] Assignee: Chiron Corporation, Emveryville, Calif.

[21] Appl. No.: 268,656

[22] Filed: Jun. 29, 1994

Related U.S. Application Data

[63] Continuation of Ser. No. 76,289, Jun. 11, 1993, abandoned, which is a continuation of Ser. No. 675,922, filed as PCT/US89/04821, Nov. 3, 1989, abandoned, which is a continuation-in-part of Ser. No. 267,408, Nov. 4, 1988, abandoned.

[51] Int. Cl.$^6$ ............................ C12N 15/09; C12N 15/81
[52] U.S. Cl. ................... 435/69.4; 435/69.7; 435/172.3; 435/254.2; 514/2; 536/23.51; 530/399
[58] Field of Search .................................. 435/69.1, 69.4, 435/69.7, 172.3; 514/2, 12; 536/23.4, 23.51, 23.5; 530/350, 399, 412

[56] References Cited

U.S. PATENT DOCUMENTS

| | | | |
|---|---|---|---|
| 4,966,848 | 10/1990 | Smith | 435/193 |
| 4,994,559 | 2/1991 | Moscatelli | 530/399 |
| 5,066,591 | 11/1991 | Hallewall et al. | 435/189 |
| 5,155,214 | 10/1992 | Baird | 530/399 |
| 5,156,949 | 10/1992 | Luciw et al. | 435/5 |
| 5,223,483 | 6/1993 | Thomas et al. | 514/12 |

FOREIGN PATENT DOCUMENTS

| | | |
|---|---|---|
| 0 237 966 | 9/1987 | European Pat. Off. . |
| 0 259 953 | 3/1988 | European Pat. Off. . |
| 0 275 204 | 7/1988 | European Pat. Off. . |
| WO85/01503 | 4/1985 | WIPO . |
| WO87/01728 | 3/1987 | WIPO . |
| WO87/05332 | 9/1987 | WIPO . |

OTHER PUBLICATIONS

Gospodarowicz et al., "Fibroblast Growth Factor," Molecular and Cellular Endocrinol. (1986) 46:187–204.

Urdea et al., "Chemical Synthesis of a Gene for Human Epidermal Growth Factor Uroqastrone and Its Expression in Yeast," Proc. Natl. Acad. Sci. USA (1983) 80:7461–7465.

Barr et al., "Antigenicity and Immunogenicity of Domains of the Human Immuno-deficiency Virus (HIV) Envelope Polypeptide Expressed in the Yeast *Saccharomyces cerevisiae*," Vaccine (1987), 5:90–101.

Gimenez-Gallego et al., "Brain-Derived Acidic Fibroblast Growth Factor: Complete Amino Acid Sequence and Homologies," Science (1985), 230:1385–1388.

Esch et al., "Primary Structure of Bovine Pituitary Basic Fibroblast Growth Factor (FGF) and Comparison with the Amino-Terminal Sequence of Bovine Brain Acidic FGF," Proc. Natl. Acad. Sci. USA (1985), 82:6507–6511.

Jaye et al., "Human Endothelial Cell Growth Factor: Cloning, Nucleotide Sequence, and Chromosome Localization," Science (1986), 233:541–545.

Abraham et al., "Human Basic Fibroblast Growth Factor: Nucleotide Sequence and Genomic Organization," EMBO J. (1986), 5:2523–2528.

Brake et al., "α-Factor-Directed Syntheis and Secretion of Mature Foreign Proteins in *Saccharomyces cerevisiae*," Proc. Natl. Acad. Sci. USA (1984) 81:4642–4646.

Cousens et al., "High Level Expression of Proinsulin in the Yeast, *Saccharomyces cerevisiae*," Gene (1987), 61:265–275.

Linemeyer et al., "Expression in *Escherichia coli* of a Chemically Synthesized Gene for Biologically Active Bovine Acidic Fibroblast Growth Factor," Bio/Technology (1987), 5:960–965.

Julius et al., "Isolation of the Putative Structural Gene for the Lysine-Arginine-Cleaving Endopeptidase Required for Processing of Yeast Prepro-α-Factor," Cell (1984), 37;1075–1089.

Story et al., "Amino-Terminal Sequence of a Large Form of Basic Fibroblast Growth Factor Isolated from Human Benign Prostatic Hyperplastic Tissue," Biochem. Biophys. Res. Comm. (1987), 142:702–709.

Hallewell et al., "Amino Terminal Acetylation of Authentic Human Cu, Zn Superoxide Dismutase Produced in Yeast," Bio/Technology (1987), 5:363–366.

Burgess et al., "Structural Evidence that Endothelial Cell Growth Factor β is the Precursor of both Endothelial Cell Growth Factor α and Acidic Fibroblast Growthh Factor," Proc. Natl. Acad. Sci. USA (1986) 83:7216–7220.

Crabb et al., "Complete Primary Stucture of Prostatropin, a Prostate Epithelial Cell Growth Factor," Biochem. (1986), 25:4988–4993.

Ueno et al., "Isolation of an Amino Terminal Extended Form of Basic Fibroblast Growth Factor," Biochem. Biophys. Res. Comm. (1986), 138:580–588.

Buntrock et al., "Stimulation of Wound Healing, Using Brain Extract with Fibro-blast Growth Factor (FGF) Activity," Exp. Path. (1982), 21:62–67.

D'Amore et al., "Endothelial Cell Mitogens Derived from Retina and Hypothalamus Biochemical and Biological Similarities," J. Cell Biol. (1984), 99:1545–1549.

Lobb et al., "Purification of Two Distinct Growth Factors from Bovine Neural Tissue by Heparin Affinity Chromatography," Biochem. (1984), 23:6295–6299.

Schreiber et al., "A Unique Family of Endothelial Cell Polypeptide Mitogens: The Antigenic and Receptor Cross-Reactivity of Bovine Endothelial Cell Growth Factor, Brain– derived Acidic Fibroblast Growth Factor, and Eye-Derived Growth Factor–II," J. Cell Biol. (1985), 101:1623–1626.

(List continued on next page.)

*Primary Examiner*—Stephen Walsh
*Assistant Examiner*—Sally P. Teng
*Attorney, Agent, or Firm*—Roberta L. Robins; Paul B. Savereide; Robert P. Blackburn

[57] ABSTRACT

Methods and compositions are provided for producing, in yeast, basic and acidic fibroblast growth factors (FGF's) that are at least partially acetylated at their amino-termini. DNA constructs containing genes coding for the FGF polypeptides under transcriptional control of a regulatable promoter are expressed in transformed host yeast cells to achieve high yields of the processed FGF's.

33 Claims, 9 Drawing Sheets

OTHER PUBLICATIONS

Baird et al., "Retina– and Eye–Derived Endothelial Cell Growth Factors: Partial Molecular Characterization and Identity with Acidic and Basic Fibroblast Growth Factors," J. Biochem. (1985), 24:7855–7860.

Lobb et al., "Purification and Characterization of Heparin–binding Heparin–binding Endothelial Cell Growth Factors," J. Biol. Chem. (1986), 261:1924–1928.

Huang et al., "Bovine Brain–Derived Growth Factor," J. Biol. Chem. (1986) 261:11600–11607.

Gospodarowicz, "Isolation and Characterization of Acidic and Basic Fibroblast Growth Factor," Meth. Enzymol. (1987), 147:106–119.

Folkman et al., "Angiogenic Factors," Science (1987), 235:442–447.

George–Nascimento et al., "Characterization of Recombinant Human Epidermal Growth Factor Produced in Yeast," Biochem. (1988), 27;797–802.

Barr et al., "Expression and Processing of Biologically Active Fibroblast Growth Factors in the Yeast *Saccharomyces cervisiae,*" J. Biol. Chem. (1988) 263:16471–16478.

Gimenez–Gallego, G. et al., *Biochem. Biophys. Res. Comm.,* 135 (2): 541–548, 1986.

Klagsbrun, M. et al., *PNAS,* 83;2448–2452, 1986.

FIG. 1

```
  1                                          10
MetAlaAlaGlySerIleThrThrLeuProAlaLeuProGluAspGlyGlySerGlyAla
ATGGCCGCCGGGAGCATCACCACGCTGCCAGCCCTGCCGGAGGACGGGGGCAGCGGCGCC
TACCGGCGGCCCTCGTAGTGGTGCGACGGTCGGGACGGCCTCCTGCCCCCGTCGCCGCGG 20                                          30
PheProProGlyHisPheLysAspProLysArgLeuTyrCysLysAsnGlyGlyPhePhe
TTCCCCCCAGGCCATTTCAAGGACCCAAAGAGACTGTACTGTAAGAACGGCGGGTTCTTC
AAGGGGGGTCCGGTAAAGTTCCTGGGTTTCTCTGACATGACATTCTTGCCGCCCAAGAAG
 40                                          50
LeuArgIleHisProAspGlyArgValAspGlyValArgGluLysSerAspProHisIle
CTGAGAATCCATCCCGACGGCAGGGTCGATGGCGTGAGAGAAGAGCGACCCTCATATC
GACTCTTAGGTAGGGCTGCCGTCCCAGCTACCGCACTCTCTCTTCTCGCTGGGAGTATAG
 60                                          70
LysLeuGlnLeuGlnAlaGluGluArgGlyValValSerIleLysGlyValCysAlaAsn
AAGCTTCAGCTGCAGGCCGAGGAGAGGGGCGTGGTCTCCATCAAGGGCGTCTGTGCCAAC
TTCGAAGTCGACGTCCGGCTCCTCTCCCCGCACCAGAGGTAGTTCCCGCAGACACGGTTG 80                                          90
ArgTyrLeuAlaMetLysGluAspGlyArgLeuLeuAlaSerLysCysValThrAspGlu
AGGTACCTGGCCATGAAGGAGGACGGCAGGCTGCTGGCCTCCAAGTGTGTCACCGACGAG
TCCATGGACCGGTACTTCCTCCTGCCGTCCGACGACCGGAGGTTCACACAGTGGCTGCTC 100                                         110
CysPhePhePheGluArgLeuGluSerAsnAsnTyrAsnThrTyrArgSerArgLysTyr
TGTTTCTTCTTCGAGAGGCTGGAGTCCAACAACTACAACACCTACCGGTCAAGGAAATAC
ACAAAGAAGAAGCTCTCCGACCTCAGGTTGTTGATGTTGTGGATGGCCAGTTCCTTTATG
120                                         130
ThrSerTrpTyrValAlaLeuLysArgThrGlyGlnTyrLysLeuGlySerLysThrGly
ACCAGCTGGTACGTCGCCCTGAAGAGGACCGGCCAGTACAAGCTGGGATCCAAAACAGGA
TGGTCGACCATGCAGCGGGACTTCTCCTGGCCGGTCATGTTCGACCCTAGGTTTTGTCCT 140                                         150
ProGlyGlnLysAlaIleLeuPheLeuProMetSerAlaLysSerOC AM Ser
CCTGGGCAGAAGGCCATCCTGTTCCTGCCCATGTCCGCCAAGTCCTAATAGTCGAC
GGACCCGTCTTCCGGTAGGACAAGGACGGGTACAGGCGGTTCAGGATTATCAGCTG
```

FIG. 2

```
       1            5                                    15
MetAlaGluGlyGluIleThrThrPheThrAlaLeuThrGluLysPhe 20                                      30
AsnLeuProProGlyAsnTyrLysLysProLysLeuLeuTyrCys 35                                      45
SerAsnGlyGlyHisPheLeuArgIleLeuProAspGlyThrVal 50                                      60
AspGlyThrArgAspArgSerAspGlnHisIleGlnLeuGlnLeu 65                                      75
CysAlaGluSerIleGlyGluValTyrIleLysSerThrGluThr 80                                      90
GlyGlnPheLeuAlaMetAspThrAspGlyLeuLeuTyrGlySer 95                                     105
GlnThrProAsnGluGluCysLeuPheLeuGluArgLeuGluGlu 110                                     120
AsnHisTyrAsnThrTyrIleSerLysLysHisAlaGluLysHis 125                                     135
TrpPheValGlyLeuLysLysAsnGlyArgSerLysLeuGlyPro 140                                     150
ArgThrHisPheGlyGlnLysAlaIleLeuPheLeuProLeuPro

154
ValSerAsp
```

EXPRESSION AND PROCESSING OF AMINO TERMINUS ACETYLATED FGF'S IN YEAST

This application is a continuation of U.S. application Ser. No. 08/076,289, filed 11 Jun. 1993, now abandoned, which is a continuation of U.S. application Ser. No. 07/675,922, filed 26 Jun. 1991, now abandoned, which was a continuation of PCT/US89/04821, filed 3 Nov. 1989, now in National Phase, which was filed in conjunction with and as a continuation in part of U.S. application Ser. No. 07/267,408, filed 4 Nov. 1988, now abandoned.

FIELD OF THE INVENTION

The present invention relates generally to the production of human fibroblast growth factors (FGF's) utilizing recombinant DNA technology, and more particularly, to the expression of authentic FGF's in yeast cells.

BACKGROUND OF THE INVENTION

FGF was first identified as a mitogenic pituitary hormone in the 1970's (Gospedarowicz, D. 1974 *Nature* 249:123–127). Thereafter, factors present in primarily brain and pituitary tissues were shown capable of stimulating the growth of a number of different cell types, including endothelial cells, fibroblast cells, retinal cells, and others. Only recently, with the cloning of genes encoding the various growth factors, has it become clear that most of the activities reside in two microheterogeneous proteins, basic and acidic FGF's (see, Gospedarowicz, D., (1986) *Mol. and Cell. Endocrin.* 46:187–204, which is incorporated herein by reference).

Basic and acidic FGF's have now been isolated from many diverse sources and by a variety of purification schemes. Although the production of cDNA and genomic clones encoding FGF precursors have demonstrated the common identity of the various growth factors, new issues have been raised concerning their biology. For example, the cDNA clones of the FGF's did not include classical signal sequences generally associated with secreted proteins. Also, various research groups have reported different NH2-terminus amino acids, as well as varying lengths of the overall FGF proteins.

In order to accurately decipher the different biological characteristics, if any, of the microheterogeneous forms of FGF, it is necessary to establish recombinant expression systems for the production of the various FGF forms. The expression systems should be capable of post-translational modification in the native fashion, including amino-terminal acetylation. Ideally, the systems will also provide for high expression levels of the proteins in forms that can be readily purified, all in an economical manner. The present invention fulfills these and other needs.

SUMMARY OF THE INVENTION

The present invention provides compositions and methods for the production of human basic and acidic FGF's in yeast, which are typically substantially amino-terminal acetylated. These authentically amino-terminal processed proteins are expressed in the yeast intracellularly at high levels (without secretion) and readily purified to substantial homogeneity. For human basic FGF polypeptides, a specific activity of at least about $9.3 \times 10^5$ units/mg was obtained; and for human acidic FGF polypeptides, a specific activity of at least about $0.61 \times 10^5$ units/mg was obtained.

Methods of the present invention for producing the authentic post-transnational modified forms of human FGF's comprise the steps of:

a) transforming yeast with an expression plasmid comprising a gene encoding an FGF of about 155 amino acids including N-terminal methionine, wherein the gene is under transcriptional control of a promoter functional in yeast;

b) culturing the transformed yeast under conditions suitable for expression, substantially without secretion, of the FGF gene, wherein N-terminus acetylated FGF polypeptides are produced; and c) separating the FGF polypeptides from the yeast culture. In this manner, typically between 30% and 100% of the FGF polypeptides are amino-terminal acetylated. The FGF polypeptides are frequently microheterogeneous, containing from about two to about five modified forms. Each of these polypeptides may be purified to homogeneity by, e.g., a heparin affinity column and/or an HPLC column.

The DNA constructs of the present invention are those capable of directing the intracellular expression in yeast of a final processed human basic or acidic FGF (1–154), and deletions thereof. The constructs can also comprise a yeast transcriptional promoter DNA region upstream from an initiation codon, which is fused to a gene encoding the desired FGF. The gene is typically followed downstream by a transcription terminator. Generally, the construct is not capable of directing the secretion of polypeptides from the transformed yeast cell host.

The compositions containing the acetylated human FGF's of the present invention typically have essentially all the primary structural conformation and one or more of the naturally associated biological properties of native FGF's. These compositions will be substantially free from bacterial or other mammalian proteins, and will typically not include an initial methionine amino acid residue.

BRIEF DESCRIPTION OF THE FIGURES

FIG. 1 shows the amino acid sequence and corresponding preferred synthetic nucleotide sequence for human basic FGF (1–154).

FIG. 2 shows the amino acid sequence of human acidic FGF (1–154).

DESCRIPTION OF THE SPECIFIC EMBODIMENTS

Figure 3A:
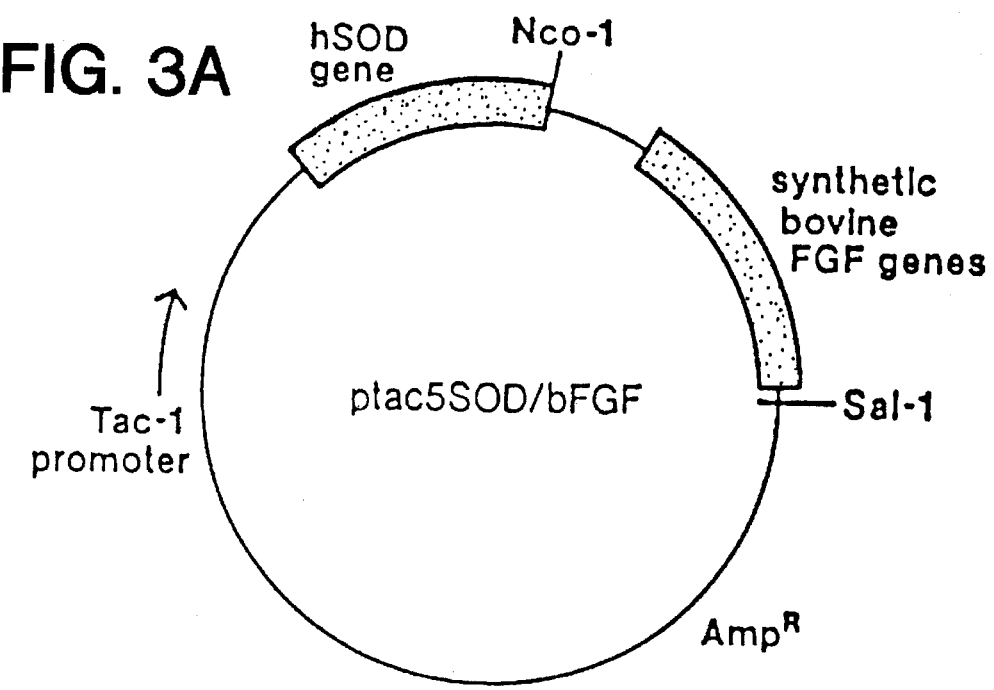
FIGS. 3(a)–(c) are schematic representation of plasmid constructions for the expression of bovine and human FGF's. (a) ptac5SOD/bFGF, derived from ptac5SOD, allows the transcription of hSOD, together with bovine acidic FGF (1-140) and bovine basic FGF (1-146) RNA's as dicistronic messages. (b) pAB24a/GaF-baFGF (1-140) and pAB24A/GaF-bbFGF (1-146) yeast secretion plasmids for the expression and processing of a-factor leader bFGF fusion proteins in *S. cerevisiae*. Transcription is driven by the glucose regularable ADH-2/GAPDH promoter. (c) pAB24 A/G-haFGF and pAB24 a/G-hbFGF plasmids for the glucose regularable intracellular expression of human FGF precursors. Again, transcription is driven by the ADA-2/GAPDH promoter. The parent yeast vector pAB24 contains LEU2 and URA3 genes for selection of transformants under leucine or uracil deficient conditions. Detailed DNA and encoded amino acid sequences around the promoter and secretion signal-FGF fusions are shown in FIG. 4.

Methods and compositions are provided for the efficient expression of authentic FGF polypeptides, in particular, acidic and basic FGF's that are acetylated at the aminoterminus during intracellular yeast expression. The methods employ DNA sequences encoding the amino acid sequence of the desired FGF, in conjunction with a translational initiation region optimized for expression in yeast cells. The genes are inserted into a vector capable of intracellular expression (i.e., substantially in the absence of secretion), so the FGF polypeptides are harvested only after the cells have been lysed. Thereafter, the FGF's may be purified for use in a variety of ways, including enhancing in vitro growth of susceptible cells, and as therapeutic agents.

The compositions of the present invention will typically comprise human FGF's that are acetylated. As used herein, acetylation refers to an acetyl group addition at the aminoterminus of the proteins;such as disclosed in copending, commonly assigned U.S. Ser. No. 609,412, filed Nov. 5, 1984, which is incorporated herein by reference.

Acetylation is desirable for a number of reasons, most notably to provide a product having the appropriate native structure and confirmation. Thus, for use in pharmaceutical applications, the acetylated FGF's will substantially reduce or eliminate immunogenicity when administered to a host. Further acetylated polypeptides are thought to be more stable and resistant to degradation when utilized in vivo, permitting prolonged residence in the host. Compositions of the present invention can comprise 100% acetylated polypeptides, but more typically acetylation will range from about 70% to 50%, but may be as low as 30% or less, as desired.

The FGF's of the present invention fall into two general categories, basic FGF and acidic FGF. As used herein, basic FGF's will commonly have a pI between about 9.0 and I10.0, preferably about 9.6, and be capable of binding heparin. Basic FGF is an angiogenic factor and is mitogenic for a wide variety of normal diploid mesoderm-derived and neurocrest-derived cells, including granulocytes, adrenal cortical cells, chrondocytes, myeloblasts, corneal and vascular endothelial cells, and vascular smooth muscle cells (see, U.S. Ser. No. 139,953, filed Dec. 31, 1987, which is incorporated herein by reference). In accordance with the present invention, baste FGF has been produced in various cleaved forms, but a preferred form is amino-terminal acetylated basic FGF (1-154), with the numbering beginning with the alanine residue immediately following the initiation codon, as shown for human basic FGF in FIG. 1 (see, PCT/US86/01879; published Mar. 26, 1987, the disclosure of which is incorporated here by reference).

As used herein, acidic FGF refers to a protein that has a pI substantially less than 7.0, typically about 5.0 to about 6.0, and is also capable of binding to heparin. Generally, acidic FGF is active as a mitogen on many of the same types of cells as basic FGF, such as fibroblast, vascular and corneal endothelial cells, chrondocytes, osteoblasts, myeloblasts, smooth muscle cells and glial cells. Also, similar to basic FGF, a preferred acidic FGF is about 154 amino acids when utilizing the same numbering system such, as shown for human basic FGF in FIG. 2 (See, European Application No. 87306066.9, published March 16, 1988, which is incorporated herein by reference).

Both acidic and basic FGF's are known to exist in various microheterogeneous forms, i.e., the 154 amino acids may be subject particularly to proteolysis, but to additional modifications as well. Thus, additional forms, offered by way of example and not limitation, include human acidic FGF's (9-154), (13-154) and (16-154) and human basic FGF's (9-154) and (10-154). Thus, as used herein, authentically amino-terminally processed FGF's refers to such microheterogeneous forms, some of which will typically be acetylated. Of course, those skilled in the art will recognize that the FGF's of the present invention may also be subject to allelic differences and standard mutations, such as internal deletions, additions or substitutions of many of the amino acid residues, provided one or more of the desired biological activities remain.

To prepare the FGF polypeptides of the present invention in yeast, appropriate DNA sequences encoding the polypeptides must be either isolated or chemically synthesized by assembly of nucleotide bases in accordance with standard techniques. Preferably, chemical synthesis will be utilized, wherein all the nucleotides corresponding to sequences from beth strands of the desired gene or synthesized in overlapping sections, for subsequent assemblage into full-length genes.

Once obtained, these genes are inserted into vectors, such as yeast extrachromosomal elements containing a yeast promoter, which is capable of directing internal expression of the desired proteins. These vectors will typically also include an initiation codon, fused immediately upstream from the gene, and a termination codon immediately downstream from the gene. Suitable strong promoters include alcohol dehydrogenase 1 and 2, triosephosphate isomerase, and any other well known promoters. To ensure proper acetylation, however, secretory signal sequences are typically avoided to ensure sufficient acetylation. A common yeast terminator sequence, such as the TPI-1 terminator, may also be utilized. All of these DNA fragments may be ligated in accordance with well known techniques, such as described in Maniatis et al., *Molecular Cloning: A Laboratory Manual*, Cold Spring Harbor Laboratory 1982, which is incorporated herein by reference.

After preparation of the desired DNA construct, the vector is transformed into the desired yeast host by standard techniques. A preferred host is *S. cerevisiae* with reduced protease levels, but preferably other than an NAT 1 (N-terminal acetyl transferase) minus mutant. A particularly preferred strain of *S. cerevisiae* is the one designated JSC302, which has been deposited 2 Nov. 1989 with the American Type Culture Collection, Rockville, Md. U.S.A and was given ATCC accession No. 20967. By overexpression of NAT 1 and ARD 1 (arrest defective), which apparently must be overexpressed together to provide additional acetylase activity, substantially increased acetylated FGF's can be produced. To obtain such overexpression, NAT 1 and ARD 1, under the control of strong promoters, are integrated into separate hosts, which are then mated to form diploids suitable for transformation of the desired expression vector containing FGF.

The transformed yeast cells may be selected by growth on conventional complex medium, which will vary depending upon the particular vector utilized. Once selected, transformants containing the vectors are cloned, high producers selected, and then grown up in the appropriate media.

When the yeast cells have been grown to the desired density, the intracellular FGF's of the present invention may be obtained by first lysing the cells, and then isolating the desired protein by standard purification techniques. Such techniques are well known to those skilled in the art, and can include affinity chromatography (particularly, heparin based), electrophoresis, dialysis, HPLC or other column chromatography, and the like. The FGF's may be purified to homogeneity, typically at least 95% pure, and as much as 98% to 99% pure, or more.

The acidic and basic FGF's of the present invention will have substantially the same amino acid sequences as the naturally occurring proteins. As noted previously, microheterogeniety may result in cleavage of varying amino acid stretches from the protein, typically from the amino-terminal end. Five or more forms of an FGF polypeptide may be purified from a single yeast culture, but more typically, two or three forms are produced. Usually, at least about 50% or more of the FGF forms will be acetylated, with the other forms varying from a low of 2% to 5% percent, up to about 40% to 50% of the mixture.

Particularly preferred compositions contain only a single form of FGF. Such a composition may be obtained from microheterogeneous FGF preparations by additional chromotagraphy or electrophoresis steps. Alternatively, human basic FGF (9-154) is expressed in yeast without microheterogeneity.

The substantially pure FGF polypeptides of the present invention can be combined with the pharmaceutically acceptable carrier to form pharmaceutical compositions, which may be administered to patients either intravenously, subcutaneously, intramuscularly, or orally. Required doses will, of course, vary with the particular condition being treated, with the severity of the condition and with the duration of the desired treatment. Suitable concentrations will also vary widely, usually between about 1 and 50 mg/ml, preferably between about 10 to 100 mg/ml. A therapeutically effective amount sufficient to accelerate the rate of appearance and increase of new fibroblasts in vivo will be in the range of 1 to 5 mls of the concentrated preparation. Similar concentrations, but typically lower, may be used to enhance growth or viability of FGF-receptive cells in vitro, such as in cell culture.

These proteins are often administered in the form of pharmaceutically acceptable nontoxic salts, such as acid addition salts or metal complexes, e.g. zinc, iron or the like. The proteins of the present invention should be administered under the guidance of a physician. If desired, proteins may be administered in conjunction with suitable carriers, diluents in stabilizers, as well as other therapeutic agents, such as other mitogens, including platelet derived growth factor, epidermal growth factor, insulin-like factors, and any of the well known transforming growth factors, such as TGF-a, TGF-, or the like.

The purified recombinant authentic FGF's of the present invention have been shown to be active in a variety of system. These include standard assays of cell proliferation, such as fibroblasts and endothelial cells, as well as in models of angiogenesis. Thus, these FGF's can be utilized in the wide range of applications in which other FGF's have been demonstrated active. These include in vivo models of nerve regeneration, wound repair, isehemia, and corneal repair. Moreover, as a neutrophic factor capable of promoting neuron survival and differentiation, the present FGF's will permit the development of therapeutic products useful in the central and peripheral nervous systems, such as for treating cell senescence, neuronal regression, and cell death.

The following examples are offered by ways of illustration, not by limitation.

EXPERIMENTAL

I. Materials and Methods

The following general materials and methods were utilized to prepare the DNA constructs and expressed FGF proteins of the present invention. Each of the cited references is specifically incorporated herein by reference. Also, the following abbreviations are used:

baFGF refers to bovine acidic FGF, haFGF refers to human acidic FGF, bbFGF refers to bovine basic FGF and hbFGF refers to human basic FGF.

Figure 3B:
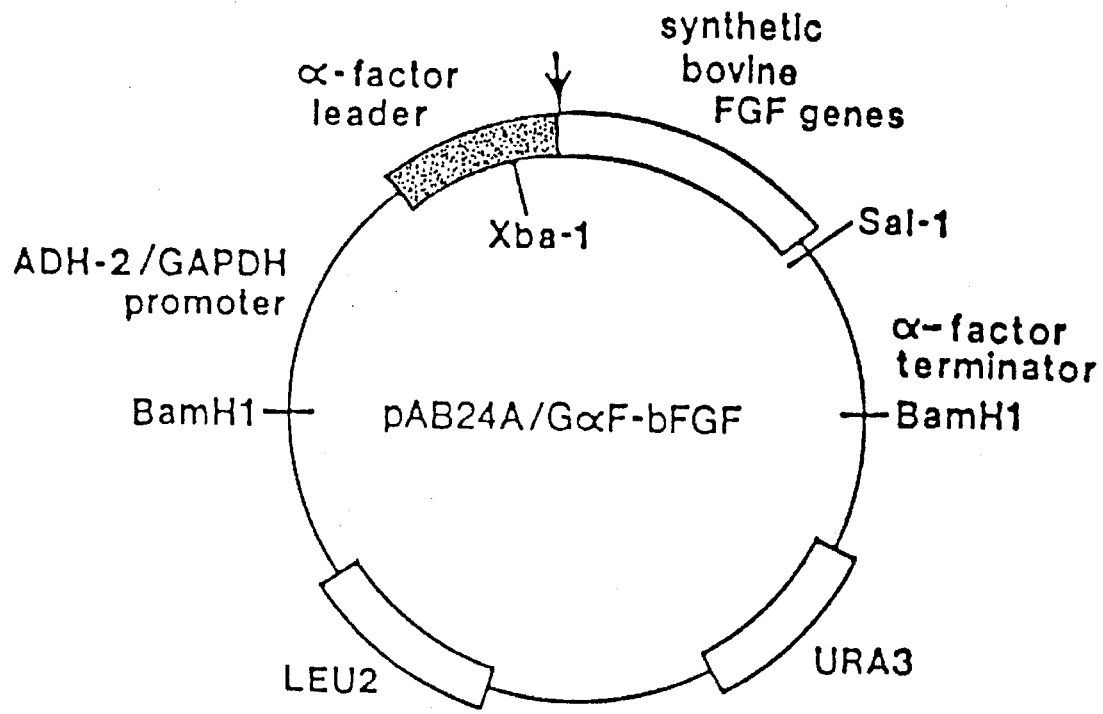
Figure 3C:
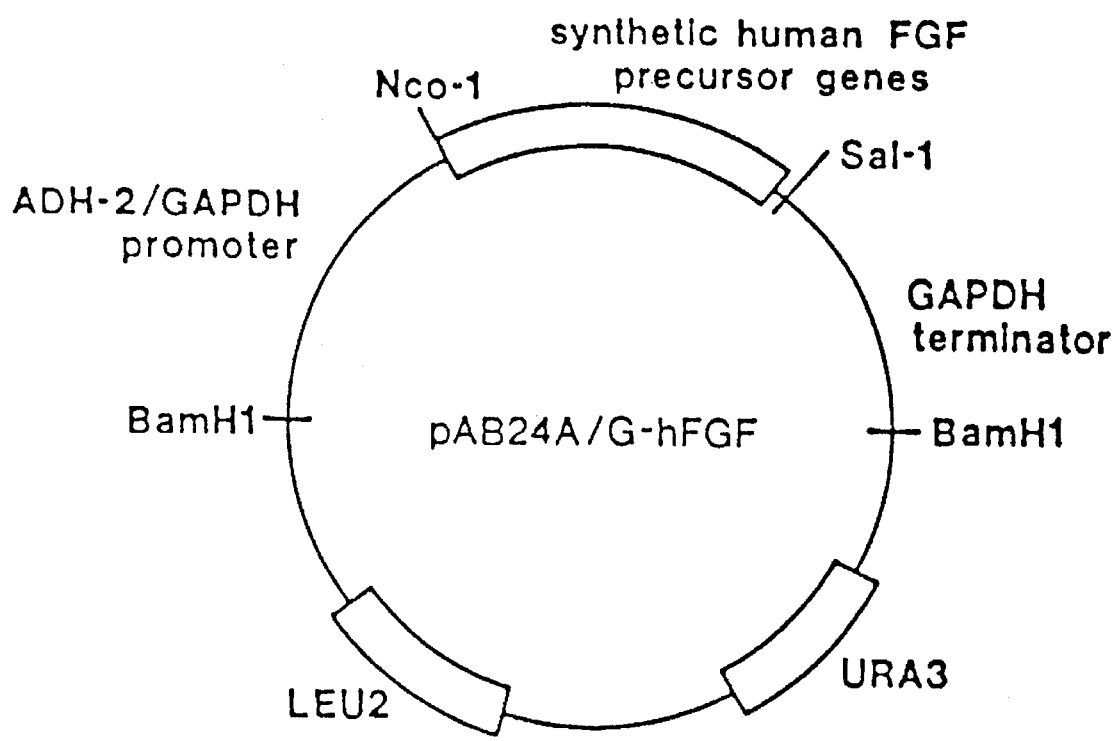

A. DNA Synthesis and Gene Assembly Oligonucleotides were synthesized by the phosphoramidite method using Applied Biosystems 380A synthesizers. Cyanoethoxyphosphoramidite intermediates (American Bionetics, Hayward, Calif.), and o-nitrophenyltetrazole activating agent (American Bionetics) were used for the synthesis of oligonucleotides varying in length between 18 and 45 bases. Typically, a full gene comprised of approximately 22 such oligonucleotides with maximum overlap between complementary oligonucleotides. Purification and phosphorylation of each oligonucleotide has been described in Urdea, M., et al., (1983) *Proc. Natl. Acad. Sci. U.S.A.* 80:7461–7465. The mixed oligonucleotides heated to 90 and allowed to cool to 25 over 3h in a buffer containing 20 mM Tris-HCl, pH 8.0, 10 mM MgC12, and 10 mM dithiothreitol. After annealing, the mixture was adjusted to 3 mM ATP. Ligation for 15 min at 25 with T4 DNA ligase (5 mL, New England Biolabs, 4×105 U/ml) was followed by ethanol precipitation and digestion with Xba-1 and Sal-1. Each synthetic bovine gene was purified by polyacrylamide gel electrophoresis on 7% acrylamide, electroeluted and cloned into Xba-1/Sal-1 digested pHG100. The corresponding human genes were similarly cloned into Nco-/Sal-1 digested pBS100 (Barr, P., et al., (1987) *Vaccine* 5:90–101). These plasmids were digested with BamH1 to release expression "cassettes", which were cloned into the BamH1 digested and alkaline phosphatase treated yeast plasmid pAB24 (FIG. 3). Gene sequences and subsequent expression vector junction sequences were verified by M13 dideoxy sequencing. For the several particularly G-C rich regions of the basic FGF genes, the dGTP analog, 7-deaza-dGTP, was used to resolve compressed areas of sequence information (Barr, P., et al., (1986) *Bio Techniques* 4:428–432).

B. Plasmids. pHg100 is a pBR322 derived plasmid analogous to pAB114 (Brake, A., et al., (1984) *Proc.. Natl.*

Figure 4:
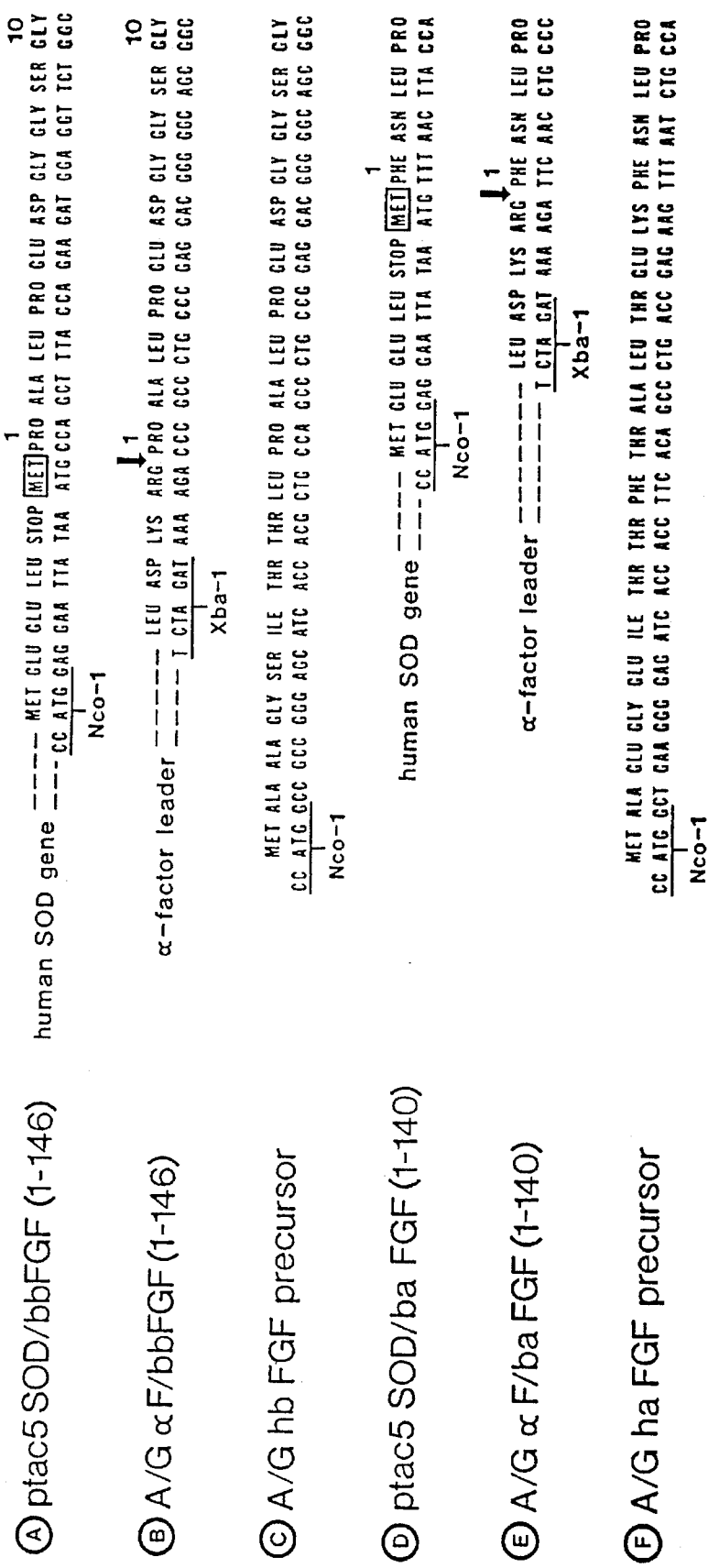
FIG. 4 depicts synthetic DNA and encoded amino acid junction sequences in basic FGF (A-C), and acidic FGF (D-F) constructions for expression in *E. coli* (A,D), secretion from *S. cerevisiae* (B,E), and for intracellular expression in *S. cerevisiae* (C,F).

*Acad. Sci. U.S.A.* 81:4642–4646). Each plasmid contains *S. cerevisiae* a-factor promoter, leader and terminator sequences flanking the a-factor structural gene in pAB114, and a synthetic human interleukin-2 (hIL-2) gene in priG100. In addition, pHG100 was modified by introduction of silent mutations encoding a unique Xba-1 cloning site immediately 5' to the mature hIL-2 coding sequence (FIG. 4). For expression studies, these a-factor leader-synthetic gene constructs were used to the ADH-2/GAPDH promoter (Barr, P., et al., (1987) *Vaccine* 5:90–101), to give vectors designated pA/Ga-factor bFGF's (FIG. 3[*b*]). pBS100 contains a BamH1 expression "cassette" consisting of the hybrid ADH-2/GAPDH promoter and the GAPDH transcriptional terminator. These control elements flank a region of the human immunodeficiency virus (HIV) env gene (Barr, P., et al., (1987) *Vaccine* 5:90–101). Cloning sites for these constructions are Nco-1, which encodes the methionine Initiation codon (FIG. 4[*c*]), and Sal-1, which is situated downstream of termination codons of the gene to be expressed. The yeast plasmid pAB24, described in Barr P., et al., (1986) *BioTechnology* 5:486–489, contains selectable markers for growth in either uracil or leucine deficient media (FIG. 3). The use of ptac5SOD for expression of hSOD fusion proteins in *E. coli* is described in Steimer, K., et al., (1986) *J. Virol.* 58:9–16.

C. Strains. For transformation and expression in *E. coli*, strain D1210 was used (Maniatis, T., et al., (1982) *Molecular Cloning, A Laboratory Manual*, Cold Springs Harbor Laboratory, Cold Spring Harbor, N.Y.). The *S. cerevisiae* strains utilized are as follows: AB110 (Mata, leu 2-3, 112ura3-52, pep4-3, his4-580, [cir]); 2150-2-3 (Mata leu2, adel, [cir]); AB116 Mata, leu2, trp-1, ura3-52, prB-1-1122, pep4-3, prC1-407, [cir]). Yeast transformations were performed as described previously in Hinnen, A., et al., (1978) *Proc. Natl. Acad. Sci U.S.A.* 75:1919–1933.

D. Purification of FGF's from recombinant bacterial and yeast cultures. Each of the recombinant FGF's was purified by heparin Sepharose chromatography (Shing, Y., et al., (1984) *Science* 223:1296–1299). Briefly, extracts from lysed bacteria or yeast were loaded directly onto columns of heparin Sepharose (Pharmacia) in Tris-CL buffer 10 mM, pH 7.0, 1 mM EDTA) and eluted with 0.6M NaCl (for acidic FGF's) and 1.0M NaCl (for basic FGF's). For *E. coli*-derived baFGF, chromatography on CM-sephadex (Pharmacia) preceded the heparin column. For elution from heparin Sepharose, NaCl gradients up to 2.0M (acidic FGF's) and 3.0M (basic FGF's) were used. For final purification of *E. coli*-derived bbFGF, gel filtration on Ultrogel AcA54 (LKB) in 20 mM Tris-CL buffer, (pH7.5, 0.1 mM EDTA, 0.3M NaCl) was also included.

The N-terminally acetylated and unblocked forms of hbFOF were separated by reverse phase HPLC on a Vydac C-4 column (0.46×25 cm). The column was equilibrated with 0.1% trifluoroacetic acid (TFA), and hbFOF's were eluded using a gradient of 32 to 34% acetonitrile. N-terminal sequence analysis of all purified FGF's was performed using an Applied Biosystems 470 A gas phase sequenator with on-line HPLC analysis of the PTH-amino acids.

E. Peptide Mapping. The two forms of hbFGF resolved by HPLC were reduced with DTT and treated with vinylpyridine to block the cysteine residues. After digestion with *Staphylococcus aureus* V8 protease, the peptides were separated by HPLC on a Vydac C-18 column (0.46×25 cm) in 0.1% TFA, using a 50 minute gradient of 10 to 40% acetonitrile. Each peak was collected and subsequently identified by amino acid composition analysis.

F. Mass Spectrometry. Protein (1-2 nmol) was dissolved in ammonium bicarbonate (150 ml, 50 mM, pH 7.8, 0.1 mM in (Ca2+) and trypsin (1% by weight) was added. Samples were incubated at room temperature. After 1 h a further 1% by weight of trypsin was added, and the digestion was continued for one more hour. Digests were terminated by freezing and lyophilization.

Assignments of protonated molecular ions of N-terminal peptides was established using a Kratos MS50S double-focusing instrument equipped with a high-field magnet, LSIMS source and a post-accelerator detector (10 KeV) in the positive ion mode (Aberth, W., et al., (1982) *Anal. Chem.* 54:2029–2034). Samples were applied to the probe tip and dried in vacuo. A matrix of thioglycerol: glycerol (1:1) containing hydrochloric acid (0.1 m) was applied prior to insertion into the source. Spectra were scanned from m/z 3000-300.

G. Mitogen Assay for FGF. The mitogenic activity of the various FGF's was assayed using density-arrested human foreskin fibroblasts (HFF), vascular endothelial cells and capillary endothelial cells. HFF cells were plated (1×104/well) in 96 well microtiter plates in Dulbecco's Modified Eagles Medium (DMEM) with 5% fetal bovine serum (Hyclone, Ogden Utah). After 5 days, dilutions of various FGF preparations were added in 10 ml of serum-free DMEM. About 18 hours later, 3H-Thymidine (1 mCi/well; Amersham, 25Ci/mmol, 103 mCi/mg), was added. Plates were then incubated for 24h and then the cultures washed with phosphate buffered saline (PBS). Trichloroacetic acid (5%) was added to the wells for 15 minutes followed by methanol for 15 minutes. The plates were then flooded with methanol, and air dried. The contents of each well were then solubilized in 50 ml 0.3N NaOH and transferred to vials containing scintillation fluid for counting. Each dilution of FGF sample was assayed in triplicate. One unit of activity is the amount of FGF required to stimulate half-maximal 3H-thymidine incorporation. The specific activity of various preparation was determined by dividing the reciprocal of the dilution yielding half-maximal incorporation by the protein concentration.

The biological activities of the FGF's were also assessed in models that monitor differentiated function. These included neurite outgrowth by PC12 cell (Gospondarowicz, D., et al., (1986) *J. Cell Physiol.* 127:121–136), prolactin release by GH3 cells (Gospodarowicz, D., et al., (1982) *J. Biol. Chem.* 257:1266–12278) and aromatase activity in fibroblasts and granulosa cells (Gospodarowicz, D. (1984) *Methods for Preparation of Media, Supplements and Substrata for Serum Free Animal Cell Culture*, pp. 275–293, Alan R. Liss, Inc., New York). The angiogenic activity of the growth factors was tested in the chick chorioallantoic membrane (Gospodarowicz, D., et al., (1984) *Proc. Natl. Acad. Sci. U.S.A.* 81:6963–6967), the rat brain (Gimbrone, M., et al., (1974) *J. Natl. Cancer Inst.* 52:413–427) and kidney capsule (Risua, W. (1986) *Proc. Natl. Acad. Sci. U.S.A.* 83:3855–3859).

II. Examples

The 435 bp and 456 bp genes for baFGF (1-140) (numbered in accordance with Gimenez-Gallego, G., et al., (1985) *Science* 230:1385–1388) and bbFGF (1-146) (numbered in accordance with Esch, F., et al., (1985) *Proc.*

*Natl. Acad. Sci. U.S.A.* 82:6507–6511), respectively, were synthesized. The constructs incorporated unique restriction enzyme targets for Hind-III and Nar-1 close to the 5'-end of the baFGF and bbFGF genes, respectively. This allowed the facile transfer of each gene into the desired expression systems, using synthetic adapters. The haFGF precursor gene (Jaye, M., et al., (1986) *Science* 233:541–545) was similarly synthesized and cloned using oligonucleotides of 29 to 44 bases in length. Since mature bovine and human basic FGF's differ in only two amino acids, only seven new molecules of between 18 and 43 bases were syntesized for the synthetic hbFGF precursor gene. These were ligated, along with the appropriate, previously synthesized oligonucleotide sequences, to give the hbFGF gene (Abraham, J., et al., (1986) *EMBO J.* 5:2523–2528).

EXAMPLE 1

Bovine FGF Gene Expression.

The synthetic genes for bbFGF (1-146) and baFGF (1-140) were expressed in *E. coli* using a two cistron message driven by the tac-1 promoter (Hallewell, R., et al., (1986) *Nucleic Acids Res.* 13:2017–2033) (FIG. 3[a]). It has been shown previously that the use of two cistron messages can overcome translation initiation problems that have been attributed to the formation of stem-loop structures around the ribosome binding site (Schoner, B., et al., (1984) *Proc. Natl. Acad. Sci. U.S.A.* 81:5403–5407). The highly expressed human superoxide dismutase (hSOD) gene to provided the first cistron of the message. This gene was followed by a new ribosome binding site, a stop codon, and an initiation codon for each of the bovine FGF genes (FIG. 4). IPTG induction of *E. coli* strain D1210 cells transformed with these plasmids allowed the moderate level expression of bovine FGF's).

These genes were also expressed as fusions with the yeast a-factor mating pheromone leader sequence (Brake, A., et al., (1984) *Proc. Natl. Acad. Sci. U.S.A.* 81:4642–4646). Synthetic adapters were used to fuse each gene to sequences encoding this secretion and processing signal (FIG. 4). This hybrid gene was flanked by the glucose regulatable alcohol dehydrogenase-2 (ADH-2)/glyceraldehyde-3-phosphate dehydrogenase (GAPDH) hybrid promoter described in Cousens L., et al., (1987) *Gene(Amst.)* 61:265–275 and Barr P., et al., (1987) *J. Exp. Med.* 165:1160–1171, and the a-factor transcriptional terminator (Brake, A., et al., (1984) *Proc. Natl. Acad. Sci. U.S.A.* 81:4642–4646). In each case, secreted FGF's were detected in the yeast supernatants by SDS-PAGE analysis of precipitated protein from TCA treated media and by bioassay.

In order to accurately define N-terminal amino acid structures and specific activities of each recombinant bovine FGF, each protein, was purified from both *E. coli* cells and *S. cerevisiae* culture media. This was accomplished by heparin-Sepharose chromatography. Using the procedure, bovine FGF samples of greater than 98% purity were obtained. N-terminal amino acid sequence analysis was performed on each of these purified Samples, and the results are shown in Table 1.

A homogeneous N-terminus was only observed in baFGF (1-140) expressed in *E. coli*. However, even this polypeptide did not represent an authentic baFGF(1-140) molecule, in that, as reported previously for baFGF expressed in *E. coli* (Linemeyer, D., et al., (1987) *Biotechnology* 5:960–965), the initiation codon derived N-terminal methionine was not removed in vivo. The *E. coli* derived bbFGF(1-146), although quantitatively processed with regard to methionine removal, was further degraded to a heterogeneous mixture of bbFGF species (Table 1). Similarly, both bovine FGF's were shown to have heterogeneous N-termini when secreted and purified from yeast. In addition to the natural cleavage at the paired basic amino acid processing site, mediated by the kex-2 gene product (Julius, D., et al., (1984) *Cell* 37:1075–1089), baFGF was further degraded at the N-terminus (Table 1). Also, secreted bbFGF was found to contain a major species which included the processing site-derived arginine in addition to authentic bbFGF(1-146) (Table 1). We ascribe this unusual processing to an inability of kex-2 protease to efficiently mediate the required cleavage between arginine and proline. The cleavage between lysine and arginine observed is most probably mediated by a yeast protease other than kex-2.

EXAMPLE 2

Human FGF precursor expression.

Because of the N-terminal heterogeneity of the recombinant bovine FGF's, the corresponding human FGF's were expressed as precursor forms using an intracellular yeast expression system. Using initiation codons predicted from protein analysis (Story, M., et al., (1987) *Biochem. Biophys. Res. Commun.* 142:702–709) and DNA sequence data for haFGF (ECGF) (Jaye, M., et al., (1986) *Science* 233:541–545) and hbFGF (Abraham, J., et al., (1986) *EMBO J.* 5:2523–2528) respectively, the synthetic precursor genes were fused directly to the ADH-2/GAPDH hybrid promoter (FIG. 4[c]). Plasmids containing these sequences (FIG. 3[c]) were used to transform yeast under conditions of leucine selection. Induction of FGF gene expression occurred concomitantly with depletion of glucose in the yeast media during culture growth (Cousens L., et al., (1987) *Gene(Amst.)* 61:265–275). Cells were harvested and analyzed for FGF expression as above. Since FGF's are cell associated in mammalian in vitro models, supernatants of these cultures were examined for exported FGF. In each ease, we found FGF polypeptides only in the soluble fraction of the disrupted yeast cells. As with mammalian system, culture media contained very little FGF (less than about 5% of total).

EXAMPLE 3

Sequence analysis of human FGF's expressed in yeast. The soluble haFGF and hbFGF polypeptides were readily purified using heparin-Sepharose. The effects of endogenous yeast vacuolar proteases on haFGF expression were studied using the pep4-3 wild type strain 2150. A clear difference in gel electrophoretic mobility between haFGF expressed in AB116 versus that from 2150 was found. Accordingly, each purified hFGF was subjected to N-terminal sequence analysis and mass spectrometry. The haFGF precursor was found to be quantitatively blocked at the N-terminus, as was LSOD (Hallewell, R., et al., (1987) *Biotechnology* 5:363–366). Mass spectral analysis of tryptic fragments of this polypeptide showed a protonated molecular ion corresponding to the acetylated N-terminal peptide Ac-AEGEITTFRALTEK at m/e 1552. No peptide corresponding to m/e 1510 (unblocked N-terminus) was observed. Thus, as with natural hSOD, yeast derived recombinant hSOD (Hallewell, R., et al., (1987) *Biotechnology* 5:363–366), natural haFGF (ECGF) (Burgess, W., et al., (1986) *Proc. Natl. Acad. Sci. U.S.A.* 83:7216–7220) and baFGF (prostatropin) (Crabb, J., et al., (1986) *Biochemistry* 25:4988–4993), the blocking group was shown to be the acetyl moiety. This data, together with amino acid sequence analysis, also showed that endogenous yeast methionyl aminopeptidase was able to efficiently cleave the initiation codon-derived methionine residue prior to acetylation.

The haFGF purified from yeast strain 2150, was shown to be a mixture of three major species cleaved after residues Phe8 (26%), Thr12 (11%), Phe15 (7%) together with the blocked precursor (54%). This observation underscores the susceptibility of N-terminal amino acid sequences of FGF's to proteolysis by aspartyl proteases, such as reported in bbFGF (Klagsbrun, M., et al., (1987) *Proc. Natl. Acad. Sci. U.S.A.* 84:1839–1842).

Purification and analysis of the expressed human basic FGF precursors showed that the N-terminal methionine was quantitatively removed. Surprisingly, however, despite the homology between the FGF's in their N-termini, experiments in peptide mapping, quantitative amino acid sequence analysis and mass spectrometry showed that hbFGF was only partially modified by acetylation. Thus, reverse phase HPLC of heparin sepharose-purified hbFGF resulted in the isolation of two distinct forms of the polypeptide in approximately equimolar proportions. Isolation and identification of V8 protease-derived peptides showed that the difference occurred in the N-terminal peptide. When tryptic digests of the hbFGF mixture were analyzed by mass spectrometry, a protonated molecular ion corresponding to the acetylated N-terminal peptide Ac-AAGSITTLPALPEDGGSGAFPPGHFK was observed at m/e 2537. In addition, the unblocked species was observed at m/e 2495. In agreement with the HPLC data, relative peak heights indicated that the two species were present in roughly equimolar quantities. This situation in some way mimics the results of isolation of basic FGF's from mammalian tissue in that hbFGF from human benign prostatic hyperplastic tissue was found to contain the unblocked N-terminus (Story, M., et al., (1987) *Biochem. Biophys. Res. Commun.* 142:702–709). Material isolated and purified from a human hepatoma was, however, found to be blocked (Klagsbrun, M., et al., (1987) Proc. Natl. Acad. Sci. U.S.A. 84:1839–1842), as was a similar higher molecular weight bbFGF from bovine pituitary (Ueno, N., et al., (1986) *Biochem. Biophys. Res. Commun.* 138:580–588).

EXAMPLE 4

Biological activities of recombinant FGF's.

In order to quantitatively assess the specific activity of each polypeptide or mixture of related polypeptides, their mitogenic activity for human foreskin fibroblasts was assayed. The specific activities of the various preparations are shown in Table 1. The capacity of the recombinant proteins to stimulate endothelial cell proliferation is indistinguishable from that of the native mitogens. The recombinant hbFGF was also tested and shown to be active in assays of angiogenesis, neurite outgrowth, neuronal survival in vitro and on the regulation of differentiated function of granulosa cells and fibroblasts.

EXAMPLE 5

Construction of modified ("short") rhbFGF.

Human baste FGF's (9-154) and (10-154) can be prepared by modifying the N-terminus of the plasmid pAB24 A/G-hbFGF to remove the initial eight and nine amino acids, respectively. The plasmid was treated to excise the Nco-1 to Nar-1 fragment, and the following synthetic oligonucleotides were inserted, each having the Nco-1 and Nar-1 overhangs:

```
                   MetProAlaLeuProGluAspGlyGlySerGly
hbFGF (9-154)    CATGCCAGCCCTGCCGGAGGACGGGGGCAGCG
                 GGTCGGGACGGCCTCCTGCCCCCGTCGCCGC

MetAlaLeuProGluAspGlyGlySerGly
hbFGF (10-154)   CATGGCCCTGCCGGAGGACGGGGGCAGCGG
                 CGGGACGGCCTCCTGCCCCCGTCGCCGC
```

These plasmids are capable of expressing the desired FGF forms in yeast, with hbFGF (10-154) exhibiting partial acetylation, and the genes can be expressed using the ADH2/GAPDH promoter, as described previously (Barr, et al., *J. Biol Chem.*, 2.63.:16471–16478, 1988).

TABLE 1

| Construction (See FIG. 1) | Bacterial or Yeast Strain | N-terminal amino acid sequences and approximate relative abundances | | Specific activity (U/mg × 10⁻⁵) |
|---|---|---|---|---|
| A bbFGF | E. coli D1210 | 1<br>Pro—Ala—Leu—<br>Ala—Leu— | (54%)<br>(46%) | 8.9 |
| B bbFGF | S. cerevisiae AB110 | −1    1<br>Arg—Pro—Ala—Leu—<br>Pro—Ala—Leu | (74%)<br>(26%) | 8.0 |
| C hbFGF | S. cerevisiae AB116 | Acetyl-Ala—Ala—<br>Ala—Ala— | (50%)<br>(50%) | 9.3 |
| D baFGF | E. coli D1210 | 1<br>Met—Phe—Asn—Leu— | (100%) | 0.52 |
| E baFGF | S. cerevisiae AB110 | 1<br>Phe—Asn—Leu—<br>Asn—Leu—<br>Leu— | (90%)<br>(5%)<br>(5%) | 1.8 |
| F (i) haFGF | S. cerevisiae AB116 | 1<br>Acetyl-Ala—Glu— | (100%) | 0.61 |

TABLE 1-continued

| Construction (See FIG. 1) | Bacterial or Yeast Strain | N-terminal amino acid sequences and approximate relative abundances | | Specific activity (U/mg × 10⁻⁵) |
|---|---|---|---|---|
| (ii) haFGF | S. cerevisiae 2150-2-3 | 1<br>Acetyl-Ala—Glu—<br>Ala—Glu— | (54%)<br>(2%) | 0.31 |
| | | 9<br>Thr—Ala—Leu— | (26%) | |
| | | 13<br>Glu—Lys—Phe— | (11%) | |
| | | 16<br>Asn—Leu—Pro— | (7%) | |

EXAMPLE 6

Expression and characterization of the "short" rhbFGF's.

Figure 5:
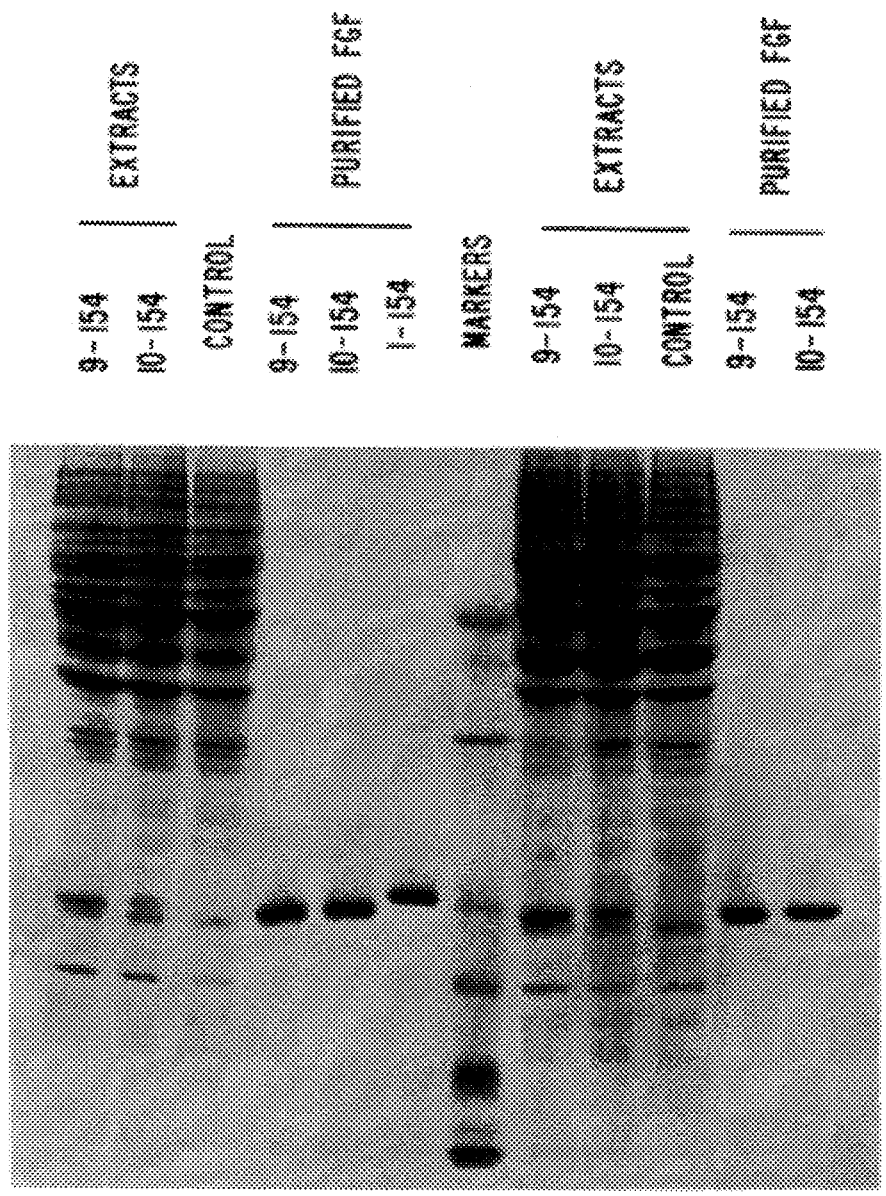
FIG. 5 shows SDS Gel analysis of "short" rhbFGF expression. Extracts were made by glass bead lysis of yeast cells, and subjected to 1 hour at 50,000 rpm in an ultracentrifuge. Aliquots of these clarified extracts were analyzed by SDS gel electrophoresis. The rhbFGF's were purified by chromatography on a Heparin 5-PW HPLC column, and portions of the purified protein also electrophoresed.

These rhbFGF's were expressed internally in yeast as taught in Example 5 and purified starting with cell breakage and centrifugation. As shown in FIG. 5, rhbFGF was visible on a gel or the clarified yeast extracts, but absent from cell extracts containing a control plasmid. These proteins were purified by Heparin-5PW HPLC chromatography, which yielded nearly homogeneous material, FIG. 5. When more rhbFGF (about 15 ug) was electrophoresed to detect any minor bands, two very minor, high molecular weight contaminants were evident, but no equivalent of 19.5 kDa rhbFGF was seen. These short rhbFGF's bound normally to heparin, indicating that these short rhbFGF's are active. The expression levels were higher in the 9-154 form than in the 10-154 form. For both forms, JSC302 is the preferred yeast host, as for 1-154 rhbFGF. The expression of rhbFGF 9-154 in JSC302 was estimated to be 24 mg per liter of yeast culture, which is in the same range of expression as rhbFGF 1-154 (about 35 mg/liter).

Figure 6:
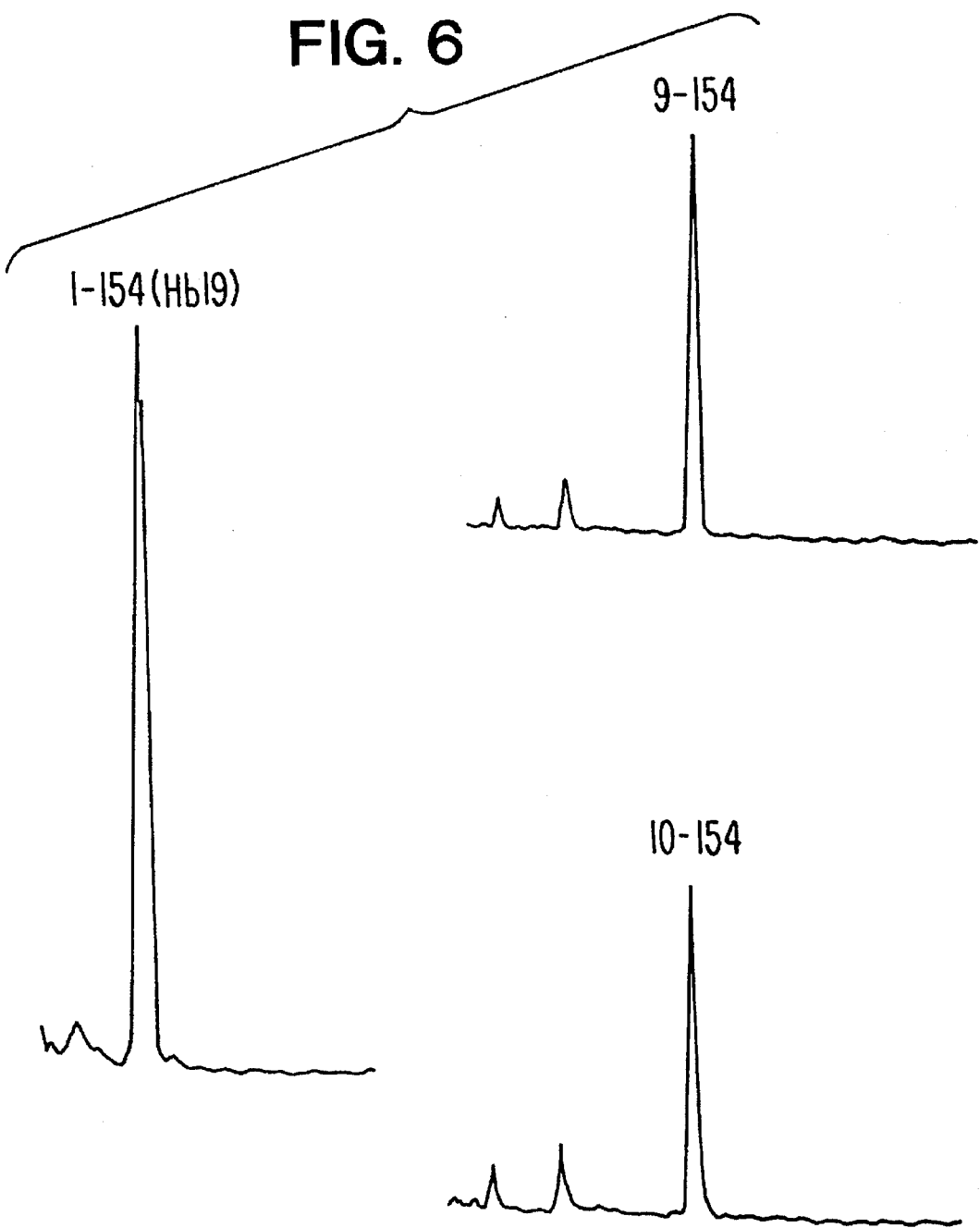
FIG. 6 shows reverse phase HPLC analysis of "short" rhbFGF's 9-154 and 10-154. A portion of the purified rhbFGF's were analyzed by chromatography on a Vydac C-4 reverse phase column at room temperature.

The purified rhbFGF 9-154 and rhbFGF 10-154 form JSC302 cells were analyzed by C-4 reverse phase chromatography. As seen in FIG. 6, both proteins eluted as a single major peak, and at approximately the same percentage of acetonitrile as rhbFGF 1-154. Two small early peaks are also evident, which are almost certainly disulfide-bonded forms of rhbFGF. Most significant, however, is that the main rhbFGF peak is a sharp peak, and not a doublet like the full length 1-154 rhbFGF. Amino terminal sequencing of the first 22 residues of the 9-154 form shows the expected sequence of "PALPEDGGSGAFPPGHFKDAPKR". No minor sequences were detected. Thus, it appears that the 9-154 form has a homogeneous N-terminus, and the sharp HPLC peak suggests that there may be no significant microheterogeneity. The 9-154 rhbFGF has an N-terminal proline which is not expected to be acetylated, while the 10-154 form begins with alanine, a preferred residue for acetylation.

EXAMPLE 7

Identification of the 19.5 kDa rhbFGF.

Figure 7A:
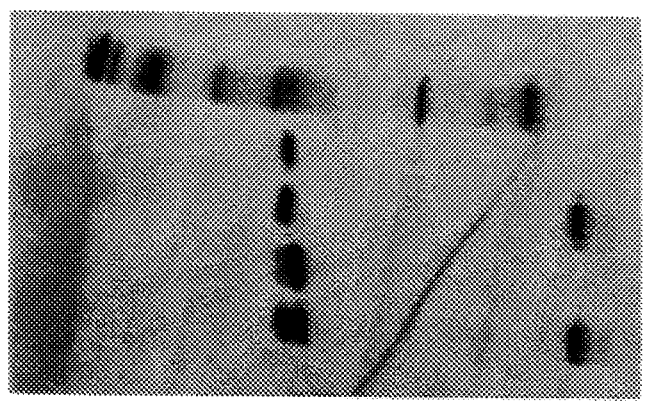
FIG. 7 shows treatment of rhbFGF with alakaline phosphatase. Aliquots of gel-purified 17.5 kDa and 19.5 kDa rhbFGF were incubated for 2 hours at 37° C. in the presence or absence of calf intestinal alkaline phosphatase, mixed with sample buffer and electrophoresed on a 15% SDS gel.
Figure 7B:
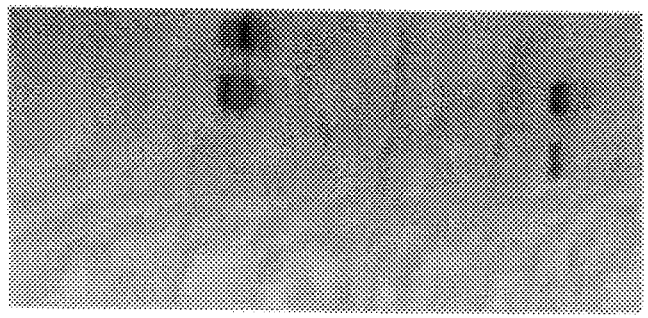

The 19.5 kDa form of rhbFGF is a minor species that migrates at a slower rate than the major rhbFGF 17.5 kDa form. Samples of gel-purified 17.5 kDa and 19.5 kDa rhbFGF were incubated with calf alkaline phosphatase to test directly whether phosphorylation causes the reduced mobility of 19.5 kDa rhbFGF. As seen in FIG. 7, this treatment had no effect on the 17.5 kDa, but shifted a portion of 19.5 kDa to 17.5 kDa form. On the righthand side of FIG. 7, electrophoresis of samples of 19.5 kDa after the alkaline phosphatase treatment shows that a high proportion of the 19.5 kDa converted to 17.5 kDa. (Since phosphoproteins are actually poor substrates for alkaline phosphatase, it is not surprising that all of the 19.5 kDa rhbFGF was not converted to the 17.5 kDa form.) This experiment shows that phosphorylation is the cause of the aberrant electrophorectic mobility of 19.5 kDa rhbFGF.

EXAMPLE 8

Improved separation of acetylated from unacetylated rhbFGF.

Figure 8:
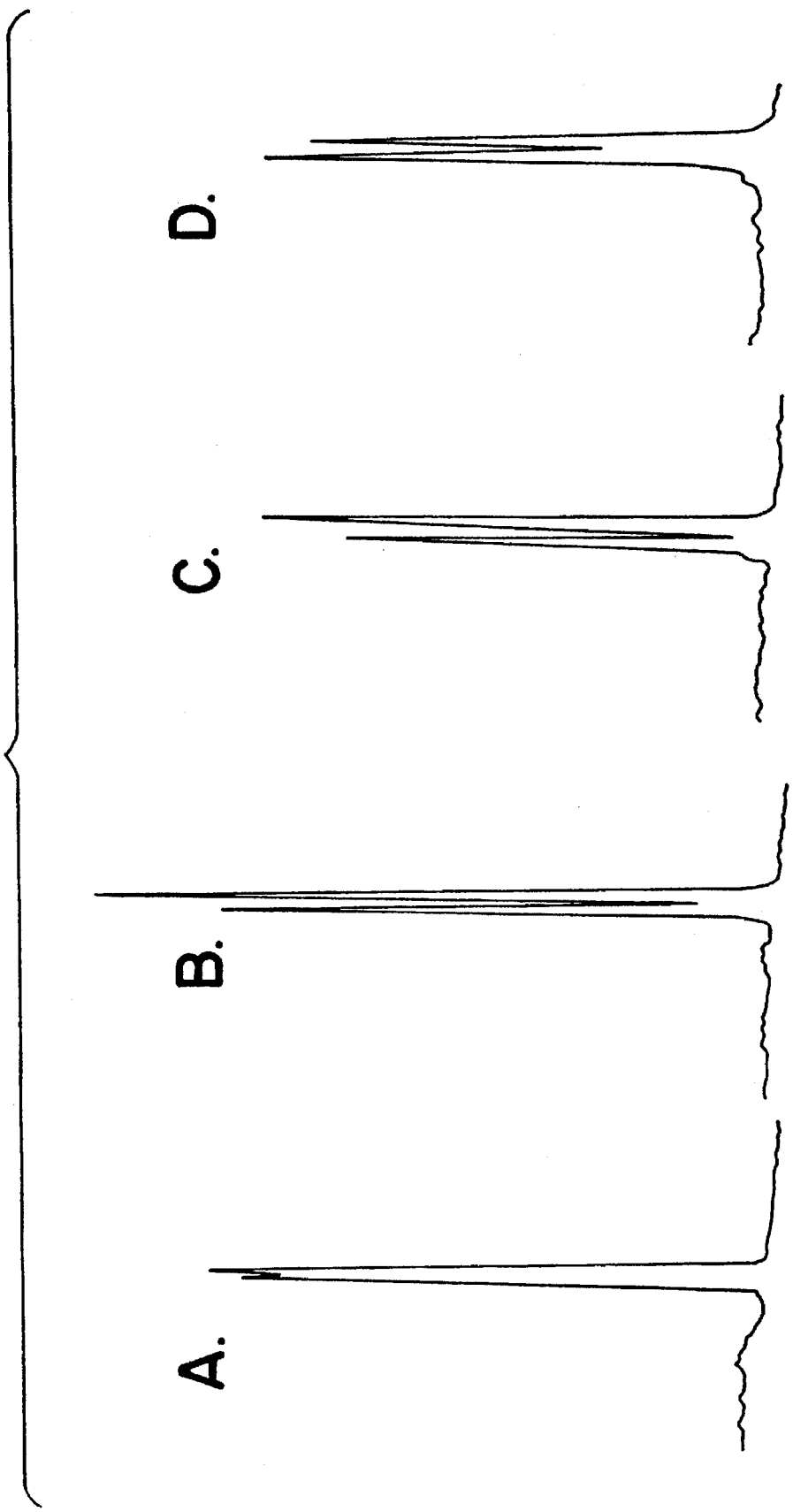
FIG. 8 shows reverse phase HPLC of rhbFGF at elevated temperature. Parts A-C, aliquots of rhbFGF (Lot Hb16) were analyzed by chromatography on a Vydac C-4 column at room temperature (Part A), and at 50° C. (Parts B and C). Part C shows a more shallow gradient than A and B. In Part D, a sample of rhbFGF (Lot Hb19) was analyzed at 50° C. on a Polymer Labs PLRP-S, 300 Angstrom column.

Although reverse phase HPLC on a TFA/acetonitrile on a Vydac C-4 column with a very shallow gradient is capable of resolving the two forms of rhbFGF, the separation at room temperature is poor and does not approach baseline resolution (FIG. 8A). As shown in FIG. 8B and C, simply using the TFA/acetonitrile buffers and the Vydac C-4 column at 50° C. resulted in near baseline separation of the two rhbFGF's. Unfortunately, the Vydac C-4 column was unable to withstand the elevated temperatures for longer than one day.

Polymer-based reverse phase columns, Polymer PLRP-S, 0.46×25 cm, 300 Angstrom pore size were tested in this system. As seen in FIG. 8D, the separation of the two rhbFGF's on the PLRP-S column at 50 ° C. was much improved over the Vydac C-4 at room temperature, and the polymer-based column was better able to withstand high temperature. Resolution of acetylated and unacetylated rhbFGF using a polymeric reverse phase column at 50° C. should be applicable to separation of microheterogeneous short forms of rhbFGF.

Although the invention has been described with regard to its preferred embodiments, which constitute the best mede presently known to the inventors, it should be understood that various changes and modifications, readily apparent to one ordinary skilled in the art, maybe made without departing from the scope of the invention as set forth in the appended claims.

I claim:

1. A product comprising, substantially pure aminoterminus acetylated human basic fibroblast growth factor (FGF) having the amino acid sequence depicted at positions 10-154 inclusive of FIG. 1, said product substantially free from bacterial or other mammalian proteins.

2. A product comprising substantially pure aminoterminus acetylated human acidic FGF (1-154) having an amino acid sequence depicted at positions 1-154 inclusive of FIG. 2, said product substantially free from bacterial or other mammalian proteins.

3. An FGF composition comprising the product according to claim 2 and at least one human acidic FGF selected from the group of FGFs consisting of FGFs (9-154), (13-154) and (16-154) having amino acid sequences depicted at positions 9-154 inclusive, 13-154 inclusive and 16-154 inclusive, respectively, of FIG. 2.

4. An FGF composition according to claim 3, wherein the acetylated human acidic FGF (1-154) comprises about 50% of the FGFs.

5. An FGF composition according to claim 4, wherein the specific activity of the human acidic FGF polypeptides is at least about $0.61 \times 10^5$ units/mg.

6. A method of producing a product comprising at least one human acidic fibroblast growth factor (FGF) polypeptide selected from the group of FGF polypeptides consisting of FGFs (1-154), (9-154), (13-154) and (16-154) having amino acid sequences depicted at positions 1-154 inclusive, 9-154 inclusive, 13-154 inclusive and 16-154 inclusive, respectively, of FIG. 2, wherein at least 30% of the FGF is amino-terminus acetylated, said method comprising the steps of:
  a) transforming yeast with an expression plasmid comprising a gene encoding said FGF polypeptide, the gene under transcriptional control of a promoter functional in yeast;
  b) culturing the transformed yeast under conditions suitable for expression of the FGF gene, wherein FGF polypeptides are not secreted; and
  c) isolating the FGF polypeptides from the yeast.

7. A method according to claim 6, wherein the product comprises human acidic FGF (1-154) having an amino acid sequence depicted at positions 1-154 inclusive of FIG. 2.

8. A method according to claim 7, wherein the method produces a product wherein at least about 50% of the FGF is amino-terminus acetylated.

9. A method according to claim 7, wherein the method produces a product comprising substantially all amino-terminus acetylated human acidic FGF.

10. A method according to claim 9, wherein the FGF polypeptides are purified with a heparin affinity column.

11. A method according to claim 9, wherein the FGF polypeptides are purified with an HPLC column.

12. A method according to claim 6, wherein said method produces a product comprising about two to five forms of amino-terminus acetylated human FGF polypeptides.

13. A method according to claim 6, further comprising purifying the FGF polypeptides to substantial homogeneity such that a single microheterogeneous FGF form is present.

14. A method according to claim 13, wherein amino-terminus acetylated FGF polypeptides are separated from non-acetylated FGF polypeptides.

15. A method according to claim 6, further comprising treating the FGF polypeptides with phosphatase enzyme subsequent to step c.

16. The method according to claim 6, wherein said yeast is strain JSC302.

17. A DNA construct capable of directing the intracellular expression in yeast to yield amino-terminus acetylated acidic fibroblast growth factor (FGF) (1-154) having an amino acid sequence depicted at positions 1-154 inclusive of FIG. 2, said DNA construct comprising a yeast transcriptional promoter DNA region upstream from an initiation codon fused to a gene encoding said FGF, the gene followed downstream by a transcription terminator, wherein said construct is not capable of directing the secretion of said polypeptides from the yeast.

18. A DNA construct according to claim 17, wherein the promoter is glucose regulatable.

19. A DNA construct according to claim 18, wherein the promoter is alcohol dehydrogenase-2/glyceraldehyde-3-phosphate dehydrogenase.

20. A yeast host cell transformed with the DNA construct of claim 17.

21. A DNA construct capable of directing the intracellular expression in yeast to yield amino-terminus acetylated basic fibroblast growth factor (FGF) (10-154) having an amino acid sequence depicted at positions 10-154 inclusive of FIG. 1, said DNA construct comprising a yeast transcriptional promoter DNA region upstream from an initiation codon fused to a gene encoding said FGF, the gene followed downstream by a transcription terminator, wherein said construct is not capable of directing the secretion of said polypeptides from the yeast.

22. A yeast host cell transformed with the DNA construct of claim 21.

23. A DNA construct according to claim 21, wherein the promoter is glucose regulatable.

24. A DNA construct according to claim 21, wherein the promoter is alcohol dehydrogenase-2/glyceraldehyde-3-phosphate dehydrogenase.

25. A DNA construct capable of directing the intracellular expression in yeast to yield amino-terminus acetylated acidic fibroblast growth factor (FGF) (9-154) having an amino acid sequence depicted at positions 9-154 inclusive of FIG. 2, said DNA construct comprising a yeast transcriptional promoter DNA region upstream from an initiation codon fused to a gene encoding said FGF, the gene followed downstream by a transcription terminator, wherein said construct is not capable of directing the secretion of said polypeptides from the yeast.

26. A yeast host cell transformed with the DNA construct of claim 25.

27. A DNA construct capable of directing the intracellular expression in yeast to yield amino-terminus acetylated acidic, fibroblast growth factor (FGF) (13-154) having an amino acid sequence depicted at positions 13-154 inclusive of FIG. 2, said DNA construct comprising a yeast transcriptional promoter DNA region upstream from an initiation codon fused to a gene encoding said FGF, the gene followed downstream by a transcription terminator, wherein said construct is not capable of directing the secretion of said polypeptides from the yeast.

28. A yeast host cell transformed with the DNA construct of claim 27.

29. A DNA construct capable of directing the intracellular expression in yeast to yield amino-terminus acetylated acidic fibroblast growth factor (FGF) (16-154) having an amino acid sequence depicted at positions 16-154 inclusive of FIG. 2, said DNA construct comprising a yeast transcriptional promoter DNA region upstream from an initiation codon fused to a gene encoding said FGF, the gene followed downstream by a transcription terminator, wherein said construct is not capable of directing the secretion of said polypeptides from the yeast.

30. A yeast host cell transformed with the DNA construct of claim 29.

31. A method of producing a product comprising a human amino-terminus acetylated basic fibroblast growth factor (FGF) depicted at positions 1-154 inclusive, of FIG. 1, said method comprising the steps of:
  a) transforming yeast strain JSC302 with an expression plasmid comprising a gene encoding said FGF, the gene under transcriptional control of a promoter functional in said yeast strain;
  b) culturing the transformed yeast under conditions suitable for expression of the FGF gene, wherein the FGF is not secreted; and c) isolating the FGF from the yeast.

32. A method of producing a product comprising amino-terminus acetylated human basic fibroblast growth factor (FGF) having an amino acid sequence depicted at positions 10-154 inclusive, of FIG. 1, said method comprising the steps of:
 a) transforming yeast with an expression plasmid comprising a gene encoding a human basic FGF having an amino acid sequence depicted at positions 10-154 inclusive, of FIG. 1, the gene under transcriptional control of a promoter functional in yeast;
 b) culturing the transformed yeast under conditions suitable for expression of the FGF gene, wherein the FGF is not secreted; and
 c) isolating the FGF from the yeast.

33. A method of producing a product comprising a human amino-terminus acetylated basic fibroblast growth factor (FGF) depicted at positions 9-154 inclusive, of FIG. 1, said method comprising the steps of:
 a) transforming yeast strain JSC302 with an expression plasmid comprising a gene encoding said FGF, the gene under transcriptional control of a promoter functional in said yeast strain;
 b) culturing the transformed yeast under conditions suitable for expression of the FGF gene, wherein the FGF is not secreted; and
 c) isolating the FGF from the yeast.

\* \* \* \* \*